United States Patent
Mathiowitz et al.

(10) Patent No.: US 6,677,313 B1
(45) Date of Patent: *Jan. 13, 2004

(54) METHOD FOR GENE THERAPY USING NUCLEIC ACID LOADED POLYMERIC MICROPARTICLES

(75) Inventors: Edith Mathiowitz, Brookline, MA (US); Yong S. Jong, Warwick, RI (US); Gerardo Carino, Providence, RI (US); Jules S. Jacob, Taunton, MA (US)

(73) Assignee: Brown University Research Foundation, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/678,764

(22) Filed: Oct. 3, 2000

Related U.S. Application Data

(62) Division of application No. 08/675,454, filed on Jul. 3, 1996, now Pat. No. 6,248,720.
(60) Provisional application No. 60/001,365, filed on Jul. 21, 1995.

(51) Int. Cl.[7] ............................................. A61K 48/00
(52) U.S. Cl. ..................... 514/44; 435/320.1; 435/455; 424/486; 424/497
(58) Field of Search .............................. 435/320.1, 455; 424/486, 497; 514/44

(56) References Cited

U.S. PATENT DOCUMENTS

| | | |
|---|---|---|
| 3,615,024 A | 10/1971 | Michaels |
| 3,639,306 A | 2/1972 | Steinberg et al. |
| 3,943,063 A | 3/1976 | Morishita et al. |
| 4,637,905 A | 1/1987 | Gardner |
| 4,818,542 A | 4/1989 | DeLuca et al. |
| 4,861,627 A | 8/1989 | Mathiowitz et al. |
| 4,997,904 A | 3/1991 | Domb |
| 5,049,322 A | 9/1991 | Devissaguet et al. |
| 5,075,109 A | 12/1991 | Tice et al. |
| 5,288,502 A | 2/1994 | McGinity et al. |
| 5,384,133 A | 1/1995 | Boyes et al. |
| 5,407,609 A | 4/1995 | Tice et al. |
| 5,460,831 A | 10/1995 | Kossovsky et al. |
| 5,466,587 A | 11/1995 | Fitzpatrick-McElligott et al. |
| 5,474,780 A | 12/1995 | Chang |
| 5,478,744 A | 12/1995 | Sanford et al. |
| 5,478,745 A | 12/1995 | Samulski et al. |
| 5,480,914 A | 1/1996 | Meadows |
| 5,498,421 A | 3/1996 | Grinstaff et al. |
| 5,516,670 A | 5/1996 | Kuehnle et al. |
| 5,518,731 A | 5/1996 | Meadows |
| 5,531,925 A | 7/1996 | Landh et al. |
| 5,639,473 A | 6/1997 | Grinstaff et al. |
| 5,783,567 A | 7/1998 | Hedley et al. |
| 6,143,211 A | 11/2000 | Mathiowitz et al. |
| 6,235,224 B1 | 5/2001 | Mathiowitz et al. |
| 6,248,720 B1 | 6/2001 | Mathiowitz et al. |

FOREIGN PATENT DOCUMENTS

| | | |
|---|---|---|
| EP | 0 248 531 A2 | 12/1987 |
| WO | WO 93/21906 | 11/1993 |
| WO | WO 94/23699 | 10/1994 |
| WO | WO 94/23738 | 10/1994 |
| WO | WO 95/24929 | 9/1995 |
| WO | WO 95/35097 | 12/1995 |
| WO | PCT/US96/11990 | 7/1996 |

OTHER PUBLICATIONS

Hirosue et al., J. Controlled Release, 70, 231–242, 2001.*
Anderson Human gene therapy pp. 25–30 vol. 1998.*
Verma et al. Gene therapy promises, problems and prospects pp. 239–242, 1997.*
Chickering, D. et al., "Bioavailability of Bioadhesive Polyanhydride Delivery Systems", *Proc. Int. Symp. Control, Release Bioact. Mater.*, 1995, 22:169–170, #320.
Chickering, D.E. et al., "Bioadhesive microspheres: I. A novel electrobalance–based method to supply adhesive interactions between individual microspheres and intestinal mucosa", *Journal of Controlled Release*, 1995, 34:251–261.
Crystal, R.G., "Transfer of Genes to Humans: Early Lessons and Obstacles to Sucess", *Science*, 1995, vol. 270, pp. 404–410.
Duchene, D. et al., "Pharmaceutical and Medical Aspects of Bioadhesive Systems for Drug Administration", *Drug Development and Industrial Pharmacy*, 1988, 14:2&3:283–318.
Duchene, D. et al., "Principle and investigation of the bioadhesion mechanism of solid dosage forms", *Biomaterials*, 1992, 13:10:709–714.
Eldridge, J. H. et al., "Biodegradable Microspheres as a Vaccine Delivery System", *Molecular Immunology*, 1991, 28:3:287–294.
Eldridge, J. H. et al., "X Pulsatile Delivery of Vaccines", *Paperback APV*, 1993, 33:163–176.
Eldridge, J.H. et al., "Biodegradable poly(DL–lactide–co–glycolide) microspheres", *Characteristics and Use of New–Generation Adjuvants, 44th Forum in Immunology*, pp. 557–563, 1992.
Fynan, E.F. et al., "DNA vaccines: Protective immunizations by parenteral, mucosal, and gene–gun inoculations", *Proc. Natl. Acad. Sci. USA*, Dec. 1993, 90:11478–11482.
Gunzburg, W.H. et al., "Virus vector design in gene therapy", *Reviews Molecular Medicine Today*, 1995, pp. 410–417.

(List continued on next page.)

*Primary Examiner*—Dave T. Nguyen
(74) *Attorney, Agent, or Firm*—Wolf, Greenfield and Sacks, P.C.

(57) ABSTRACT

The invention involves methods and products for oral gene therapy. Genes under the control of promoters are protectively contained in microparticles and delivered to cells in operative form, thereby obtaining noninvasive gene delivery for gene therapy.

12 Claims, 1 Drawing Sheet

OTHER PUBLICATIONS

Hodgson, C.P., "Biologicals & Immunologicals Advances in vector systems for gene therapy", *Exp. Opin. on Ther. Patents*, 1995, 5(5):459–468.

Kaelble, D.H. et al., "A surface energy analysis of bioadhesion", *Polymer.*, 1977, 18:475–482.

Ledley, F.D., "Nonviral Gene Therapy: The Promise of Genes as Pharmaceutical Products", *Review Human Gene Therapy*, Sep. 1995, 6:1129–1144.

Marshall, E., "Gene Therapy's Growing Pains", *Science*, Aug. 25, 1995, 269(5227):1050–1055.

Morris, W. et al., "Potential of polymer microencapsulation technology for vaccine innovation", *Vaccine*, 1994, vol. 12, No. 5, pp. 5–11.

Orkin, S.H. et al., "Report and Recommendations of the Panel to Assess the NIH Investment in Research on Gene Therapy", *NIH*, Dec. 7, 1995, pp. 1–40.

Park, H. et al., "Physico–chemical properties of water insoluble polymers important to mucin/epithelial Adhesion", *J. of Controlled Release*, 1985, 2:47–57.

Pilewski, J.M. et al., "Adenovirus–mediated Gene Transfer to Human Bronchial Submucosal Glands Using Xenografts", *American Physiological Society*, 1995, pp. L657–L665.

Sawhney, A.S. et al., "Bioerodible Hydrogels Based on Photopolymerized Poly(ethylene glycol)–co–poly($\alpha$–hydroxy acid) Diacrylate Macromers", *Macromolecules*, 1993, 26:581–587.

Spychal, R.T. et al., "Measurement of the Surface Hydrophobicity of Human Gastrointestinal Mucosa", *Gastroenterology*, 1989, 97:104–11.

Staats, H.F. et al., "Mucosal immunity to infection with implications for vaccine development", *Current Opinion in Immunology*, 1994, 6:572–583.

* cited by examiner

METHOD FOR GENE THERAPY USING NUCLEIC ACID LOADED POLYMERIC MICROPARTICLES

This application is a divisional of application Ser. No. 08/675,454, filed Jul. 3, 1996, entitled METHOD FOR GENE THERAPY USING NUCLEIC ACID LOADED POLYMERIC MICROPARTICLES now issued as U.S. Pat. No. 6,248,720 B1 and which claims priority under 35 U.S.C. §119 to U.S. application Ser. No. 60/001,365, filed Jul. 21, 1995.

GOVERNMENT SUPPORT

This invention was made with government support under Grant/Contract No. R01-GM-47636-01A3 awarded by the National Institute of Health. The government may retain certain rights in this invention.

BACKGROUND OF THE INVENTION

The application of gene therapy for the treatment of human disease has increased steadily since the first human gene therapy trial was conducted in 1989. To date, more than one hundred gene therapy protocols and clinical trials have been approved by the Recombinant DNA Advisory Committee (RAC) for the treatment of inherited and acquired diseases. Despite the reported advances in gene therapy technology and the increase of approvals in gene therapy protocols, obstacles still remain, including the difficulty in efficient delivery of exogenous genes in vivo.

Gene therapy generally involves the introduction and expression in an animal of an exogenous gene to supplement or replace a defective or missing gene or to produce a product for treating an acquired disease. While there remains some debate about which vectors are most useful under which circumstances, the evolving challenge is not whether gene therapy will work, but rather determining which vectors are the most effective and which delivery schemes are most effective for carrying out gene therapy.

Among the difficulties with delivering exogenous genes to cells for gene therapy is the cell wall itself. Some vectors and naked DNA do not efficiently penetrate mammalian cell walls. This is less of a problem in ex vivo applications where a variety of physio/chemical and mechanical technologies have been developed for introducing genes into cells. Many of these techniques, however, cannot be applied in vivo. Another problem with in vivo delivery of genes to cells is that complex structures such as vectors containing genes under the control of promoters do not fare well in certain physiological environments and are destroyed. These larger complex DNA molecules are unlike short antisense oligonucleotides which typically are modified to protect them against physiological degradation.

The conditions that can destroy an operable gene in vivo are not the only barriers to delivery of genes for gene therapy. The preparative techniques for formulating delivery systems can be destructive to DNA as well. For example, many procedures for forming microparticles require high temperature and/or high sheer forces and/or sonication. Such conditions typically'would destroy a vector containing a gene or would result in breakage of a large piece of DNA.

Oral formulations of drugs, although most convenient to the patient, face severe obstacles to delivering the drug molecules to the target cells. This is particularly true for labile drugs such as pieces of DNA or genes. A first obstacle is the stomach. The environment of the stomach is extremely destructive to DNA, and most DNA (and especially large pieces of DNA) would not survive the environment of the stomach. Even if the DNA did survive the environment of the stomach, it then must be taken up by or passed between the cells lining the large and small intestine. Uptake of material across a mucosai epithelial barrier is a selective event, and not all molecules would be expected to be taken up by absorptive and nonadsorptive epithelial cells and/or taken up into systemic circulation. Even if this obstacle is overcome, then the DNA still must resist destruction when in general circulation. The DNA also must gain access accross the membrane of the target cell which is to be transplanted. Finally, the DNA must be presented in a fashion that is nontoxic to the subject. For example, some viral vectors have been shown to induce severe immunological responses in the recipients and some liposomes have been shown to be toxic to recipients.

U.S. Pat. No. 5,075,109, entitled "METHOD OF POTENTIATING AN IMMUNE RESPONSE", issued to Tice, is directed to methods for oral administration of a bioactive agent contained in microparticles to protect the agent from degradation during its passage through the gastrointestinal tract. The patent is particularly directed to a method of oral immunization which will effectively stimulate the mucosal immune system and overcome the problem of degradation of the bioactive ingredient during its passage through the gastrointestinal tract to the Peyer's patch. The '109 patent involves administering bioactive agents contained in microcapsules that are sized between approximately one and ten microns. The microcapsules apparently survive the environment of the stomach and are taken up by the Peyer's patches to stimulate the immune response. The '109 patent does include the term "nucleic acids" as a member of a long list of materials regarded as "bioactive agents". The '109 patent does not mention the delivery of genes, the delivery of genes under the control of a promoter or the delivery of vectors including genes. This is perhaps because the methodology employed by Tice in making the microparticles is typical of prior art fabrication techniques, that is, aggressive emulsification conditions are applied, such as would destroy large pieces of DNA, in order to form the microparticles.

In none of the prior art of which applicants are aware is there disclosed the notion of delivery in microparticles of genes under the control of promoters. Certainly, none disclose the notion of oral delivery of genes under the control of promoters.

It is an object of the invention to provide a noninvasive method of carrying out gene therapy.

Another object of the invention is to provide an oral means of carrying out gene therapy.

Another object of the invention is to provide a method for microencapsulating large pieces of DNA, such as genes under the control of promoters and vectors, in a manner which does not destroy the DNA and that produces a high yield of DNA within the microcapsule. These and other objects are achieved by the present invention.

SUMMARY OF THE INVENTION

The invention involves the discovery of a method for encapsulating oligonucleotides in a nondestructive fashion and in high yield. The invention further involves the discovery that microparticles can be used to deliver these oligonucleotides orally and in functional form, not only to intestinal epithelial cells but also to nonepithelial cells within the gastrointestinal system (e.g. Peyer's patches) and even to cells remote from the intestinal epithelium such as spleen or liver cells. The invention further involves the discovery that bioadhesive microspheres, instead of simply increasing residence time upon attachment to a mucosal epithelium, surprisingly, are: (1) taken up into the epithelial cells, including absorptive intestinal epithelial cells; (2) taken up into gut associated lymphoid tissue; and (3) even transported to cells remote from the mucosal epithelium. The microparticles containing the oligonucleotides preferably are between 10 nanometers and five microns. In some important embodiments, the microparticles have an average particle size consisting of between 100 nanometers and three microns. Most preferably, the microparticles are prepared by phase inversion nanoencapsulation. The oligonucleotides are in bioactive form when released from the microparticles.

Surprisingly, we have established that genes under the control of promoters can be protectively contained in microparticles and delivered to cells in operative form, thereby obtaining noninvasive gene delivery for gene therapy. The invention overcomes extraordinary obstacles: (1) the genes are not destroyed, disrupted or inactivated by the manufacturing technique for producing the microparticles; (2) the microparticles protect the genes from the destructive environment of the stomach; (3) the microparticles enter the target cells; (4) the microparticles cause transfection of the cells with the genes; (5) the microparticles can deliver the genes to sites remote from the mucosal epithelium, i.e. can cross the epithelial barrier and enter into general circulation, thereby transfecting cells at other locations.

According to one aspect of the invention, a method for delivering a gene to a cell of a subject for gene therapy is provided. An effective amount of bioadhesive microparticles containing an isolated gene under the control of a promoter is administered noninvasively to a mucosal epithelial surface of a subject in need of such treatment. Preferably the bioadhesive microparticles consist of microparticles having an average particles size of between ten nanometers and five microns. In one embodiment, the microparticles consist of microparticles having an average particle size of between one hundred nanometers and three microns. The preferred bioadhesive microparticles comprise polyanhydrides, most preferably poly(fumaric-co-sebacic)anhydride. Preferably, they also contain metal oxides or hydroxides. Preferably, they further contain anhydride oligomers. Most preferably the bioadhesive microparticles have bioadhesive properties at least as strong as 20:80 poly(furaric-co-sebacic) anhydride.

The microparticles can be administered non-invasively, such as by oral formulation and by aerosols for the respiratory tract. In some embodiments, the gene is delivered to and transforms an epithelial cell. In other embodiments the gene is delivered to and transforms a nonepithelial cell.

According to another aspect of the invention, a method is provided for delivering a gene to a cell of a subject for gene therapy. An effective amount of microparticles containing an isolated gene under the control of a promoter is administered orally to a subject in need of such treatment. The microparticles consist of microparticles having an average particle size of between ten nanometers and five microns. In one embodiment, the microparticles have an average particle size of between one hundred nanometers and three microns.

The microparticles may be delivered to and transfect an epithelial cell or may be delivered across such epithelial cells to nonepithelial cells which are transformed by the gene. In one embodiment the cell is a gut associated lymphatic tissue cell. In another embodiment the cell is an adsorptive epithelial cell. In yet another embodiment, the microparticle is taken up into systemic circulation and the cell transfected is a nonepithelial cell remote from the epithelial barrier, such as, for example, a spleen cell or a liver cell. It is preferred that the microparticles are bioadhesive microparticles, as described above.

According to another aspect of the invention, a method is provided for noninvasive delivery of a gene into systemic circulation of a subject for gene therapy. Microparticles containing a gene under the control of a promoter are administered noninvasively to a mucosal epithelial surface of a subject in need of such treatment. The microparticles are in an effective amount and consist of microparticles having an average particle size of between ten nanometers and five microns. In one embodiment the average particles size is between one hundred nanometers and three microns. The modes of delivery and the preferred microparticles are as described above.

According to another aspect of the invention, an article of manufacture is provided. The article of manufacture is a preparation consisting essentially of microparticles containing an isolated gene under the control of a promoter. The microparticle preferably is bioadhesive. In one embodiment the microparticles consist of microparticles having an average particle size of between ten nanometers and five microns. In other embodiments, the microparticles consist of microparticles having an average particle size of between one hundred nanometers and three microns. The preferred bioadhesive microparticles are as described above.

According to another aspect of the invention, a pharmaceutical preparation for gene therapy is provided. The preparation contains an effective amount of microparticles containing a gene under the control of a promoter, wherein the microparticles consist of microparticles having an average particle size of between ten nanometers and five microns. In some embodiments, the microparticles consist of microparticles having an average particle size of between one hundred nanometers and three microns. The preparation also can include a pharmaceutically acceptable carrier suitable, for example, for oral administration to a subject wherein the pharmaceutical preparation is formulated as an oral dosage.

The invention also involves the use of any one of the foregoing materials for gene therapy. A particularly important embodiment involves a formulation for oral administration or administration by inhalation.

These and other aspects of the invention are described in greater detail below.

DETAILED DESCRIPTION OF THE INVENTION

Figure 1:
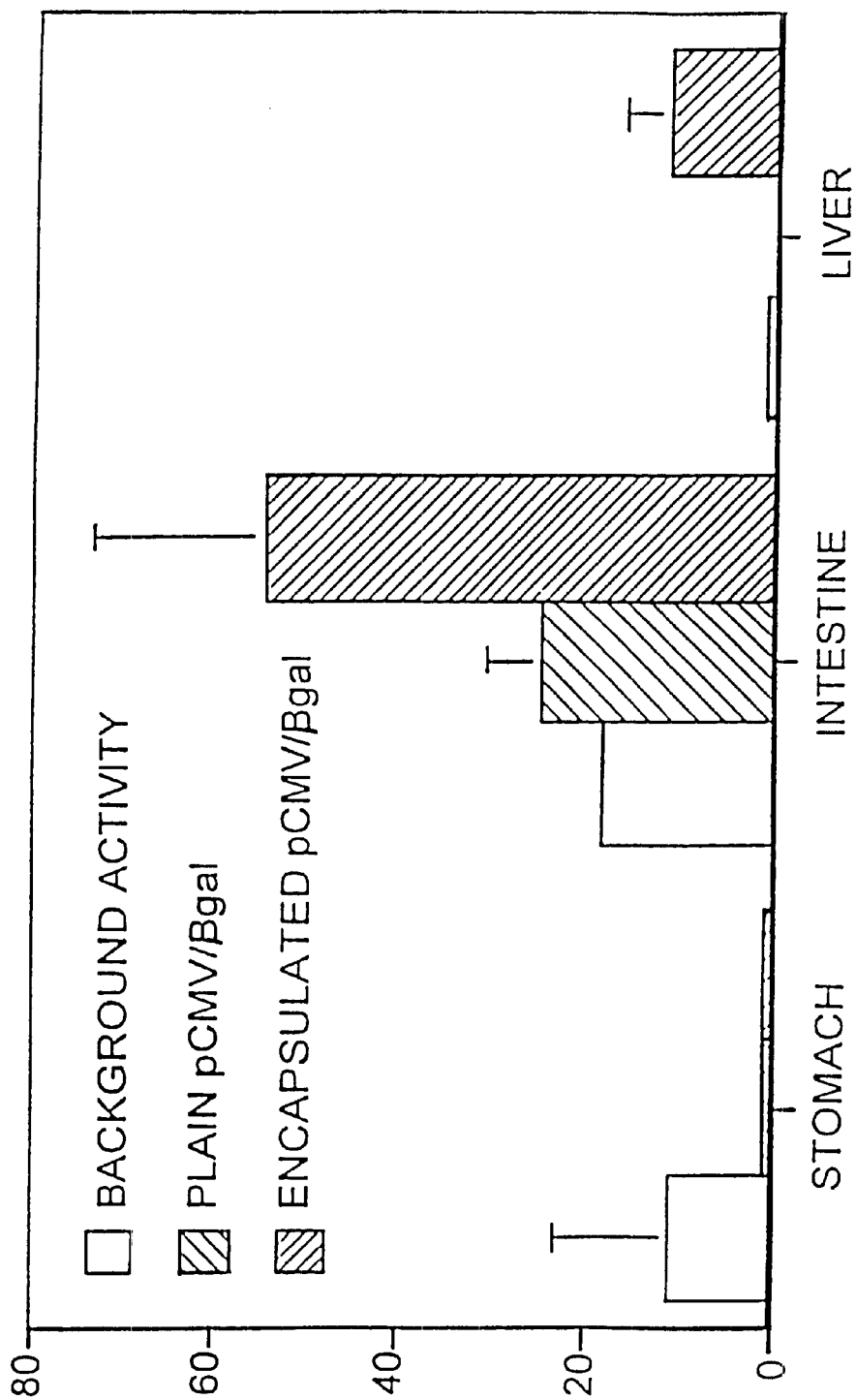
FIG. 1 is a graph depicting a luminometry assay of bacterial β-galactosidase activity in tissue homogenates resulting from oral delivery of β-galactosidase gene in microparticles.

The invention involves a gentle process for the microencapsulation of DNA, and in particular, genes under the control of promoters and vectors containing genes under the control of promoters. Microparticles, microcapsules and microspheres (here and after "microparticles") have been used in the pharmaceutical, agricultural, textile and cosmetic industry as delivery vehicles. Microparticles of a very small size have not been used for the encapsulation of genes under the control of promoters. Many microencapsulation techniques exist which can produce a variety of particle types and sizes under various conditions. Those methods that involve aggressive emulsification procedures or other procedures that would tend to break, degrade, or otherwise inactivate genes under the control of promoters are not useful according to the present invention. The present invention, in part, was prompted by the discovery of a novel method of creating microparticles having the size of five microns or less under extremely gentle processing conditions.

It has been discovered, surprisingly, that genes under the control of promoters can be delivered, in operable form, noninvasively to epithelial surfaces for gene therapy: The genes in the microparticles, not only gain access to and transfect eithelial cells, but also pass across epithelial barriers, gaining access to and transfecting cells proximal to the epithelial cells and even cells remote from the epithelial barriers, transported via systemic circulation. Even more surprising, it has been discovered that genes can be delivered to and can transfect such cells when administered orally. It is believed that the invention represents the first demonstration of oral gene delivery to intestinal epithelial cells, Peyer's patches, spleen cells, liver cells and the like.

The fabrication process, dubbed "Phase Inversion Nanoencapsulation" or "PIN", differs from existing methods of encapsulation in that it is essentially a one-step process, is nearly instantaneous, and does not require emulsification of the solvent. Under proper conditions, low viscosity polymer solutions can be forced to phase invert into fragmented spherical polymer particles when added to appropriate nonsolvents.

Phase inversion phenomenon has been applied to produce macro and microporous polymer membranes and hollow fibers. The basis for the formation of such membranes or fibers, as well as the process of the invention, depends upon the mechanism of microphase separation. A prevalent theory of microphase separation is based upon the belief that "primary" particles form of about 50 nm diameter, as the initial precipitation event resulting from solvent removal. As the process continues, primary particles are believed to collide and coalesce forming "secondary" particles with dimensions of approximately 200 nm, which eventually join with other particles to form the polymer matrix. An alternative theory, "nucleation and growth", is based upon the notion that a polymer precipitates around a core micellar structure (in contrast to coalescence of primary particles).

The fact that the present invention results in a very uniform size distribution of small particles forming at lower polymer concentrations without coalescing supports the nucleation and growth theory, while not excluding coalescence at higher polymer concentrations (e.g., greater than 10% weight per volume) where larger particles and even aggregates can be formed. (Solvent would be extracted more slowly from larger particles, so that random collisions of the partially-solvated spheres would result in coalescence and, ultimately, formation of fibrous networks.) By adjusting polymer concentration, polymer molecular weight, viscosity, miscibility and solvent:nonsolvent volume ratios, the interfibrillar interconnections characteristic of membranes using phase inversion are avoided, with the result being that microparticles are spontaneously formed. As will be seen from the examples below, as well as the following discussion, the foregoing parameters are interrelated and the adjustment of one will influence the absolute value permitted for another.

In the preferred processing method, a mixture is formed of the agent to be encapsulated, a polymer and a solvent for the polymer. The agent to be encapsulated may be in liquid or solid form. It may be dissolved in the solvent or dispersed in the solvent. The agent thus may be contained in microdroplets dispersed in the solvent or may be dispersed as solid microparticles in the solvent. The phase inversion process thus can be used to encapsulate a wide variety of agents by including them in either micronized solid form or else emulsified liquid form in the polymer solution. The loading range for the agent within the microparticles is between 0.01–80% (agent weight/polymer weight). When working with nanospheres, an optimal range is 0.1–5% (weight/weight).

The agent is added to the polymer solvent, preferably after the polymer is dissolved in the solvent. The solvent is any suitable solvent for dissolving the polymer. Typically the solvent will be a common organic solvent such as a halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as a tetrahydrofuran; ethyl acetate; diethylcarbonate; acetone; or cyclohexane. The solvents may be used alone or in combination. The solvent chosen must be capable of dissolving the polymer, and it is desirable that the solvent be inert with respect to the agent being encapsulated and with respect to the polymer.

The polymer may be any suitable mircoencapsulation material including, but not limited to, nonbioerodable and bioerodable polymers. Such polymers have been described in great detail in the prior art. A list of suitable polymers is provided below.

The working molecular weight range for the polymer is on the order of 1 kDa–150,000 kDa, although the optimal range is 2 kDa–50 kDa. The working range of polymer concentration for the phase inversion method is 0.01–50% (weight/volume), depending primarily upon the molecular weight of the polymer and the resulting viscosity of the polymer solution. In general, the low molecular weight polymers permit usage of a higher concentration of polymer. The preferred concentration range according to the invention will be on the order of 0.1–10% (weight/volume), while the optimal polymer concentration typically will be below 5%. It has been found that polymer concentrations on the order of 1–5% are particularly useful according to the methods of the invention.

The viscosity of the polymer solution preferably is less than 3.5 centipoise and more preferably less than 2 centipoise, although higher viscosities such as 4 or even 6 centipoise are possible depending upon adjustment of other parameters such as molecular weight of the polymer. The molecular weight of the polymer also will affect particle size. It will be appreciated by those of ordinary skill in the art that polymer concentration, polymer molecular weight, and viscosity are interrelated and that varying one will likely affect the others.

The nonsolvent, or extraction medium, is selected based upon its miscibility in the solvent. Thus, the solvent and nonsolvent are thought of as "pairs". We have determined that the solubility parameter ($\delta(cal/cm^3)^{1/2}$) is a useful indicator of the suitability of the solvent/nonsolvent pairs. The solubility parameter is an effective predictor of the miscibility of two solvents and, generally, higher values indicate a more hydrophilic liquid while lower values represent a more hydrophobic liquid (e.g., $\delta_i$ water=23.4 $(cal/cm^3)^{1/2}$ whereas $\delta_i$ hexane=7.3 $(cal/cm^3)^{1/2}$). We have determined that solvent/nonsolvent pairs are useful where $0<\delta$ solvent$-\delta$ nonsolvent$<6$ $(cal/cm^3)^{1/2}$. Although not wishing to be bound by any theory, an interpretation of this finding is that miscibility of the solvent and the nonsolvent is important for formation of precipitation nuclei which ultimately serve as foci for particle growth. If the polymer solution is totally immiscibile in the nonsolvent, then solvent extraction does not occur and nanoparticles are not formed. An intermediate case would involve a solvent/nonsolvent pair with slight miscibility, in which the rate of solvent removal would not be quick enough to form discreet microparticles, resulting in aggregation of coalescence of the particles.

It, surprisingly, was discovered that nanoparticles generated using "hydrophilic" solvent/nonsolvent pairs (e.g., a polymer dissolved in methylene chloride with ethanol as the nonsolvent) yielded approximately 100% smaller particles than when "hydrophobic" solvent/nonsolvent pairs were used (e.g., the same polymer dissolved in methylene chloride with hexane as the nonsolvent).

Similarly, it was discovered, surprisingly, that the solvent-:nonsolvent volume ratio was important in determining whether microparticles would be formed without particle aggregation or coalescence. A suitable working range for solvent:nonsolvent volume ratio is believed to be 1:40–1:1,000,000. An optimal working range for the volume ratios for solvent:nonsolvent is believed to be 1:50–1:200 (volume per volume). Ratios of less than approximately 1:40 resulted in particle coalescence, presumably due to incomplete solvent extraction or else a slower rate of solvent diffusion into the bulk nonsolvent phase.

It will be understood by those of ordinary skill in the art that the ranges given above are not absolute, but instead are interrelated. For example, although it is believed that the solvent:nonsolvent minimum volume ratio is on the order of 1:40, it is possible that microparticles still might be formed at lower ratios such as 1:30 if the polymer concentration is extremely low, the viscosity of the polymer solution is extremely low and the miscibility of the solvent and nonsolvent is high. Thus, the polymer is dissolved in an effective amount of solvent, and the mixture of agent, polymer and polymer solvent is introduced into an effective amount of a nonsolvent, so as to produce polymer concentrations, viscosities and solvent:nonsolvent volume ratios that cause the spontaneous and virtually instantaneous formation of microparticles.

As will be seen from the examples below, a variety of polymers have been tested in the methods of the invention, including polyesters such as poly(lactic acid), poly(lactide-co-glycolide) in molar ratios of 50:50 and 75:25; polycaprolactone; polyanhydrides such as poly(fumaric-co-sabacic)acid or P(FA:SA) in molar ratios of 20:80 and 50:50; poly(carboxyphenoxypropane-co-sebacic)acid or P(CPP:SA) in molar ratio of 20:80; and polystyrenes or PS.

Nanospheres and microspheres in the range of 10 nm to 10 μm have been produced according to the methods of the invention. Using initial polymer concentrations in the range of 1–2% (weight/volume) and solution viscosities of 1–2 centipoise, with a "good" solvent such as methylene chloride and a strong non-solvent such as petroleum ether or hexane, in an optimal 1:100 volume ratio, generates particles with sizes ranging from 100–500nm. Under similar conditions, initial polymer concentrations of 2–5% (weight/volume) and solution viscosities of 2–3 centipoise typically produce particles with sizes of 500–3,000 nm. Using very low molecular weight polymers (less than 5 kDa), the viscosity of the initial solution may be low enough to enable the use of higher than 10% (weight/volume) initial polymer concentrations which generally result in microspheres with sizes ranging from 1–10 μm. In general, it is likely that concentrations of 15% (weight/volume) and solution viscosities greater than about 3.5 centipoise discreet microspheres will not form but, instead, will irreversibly coalesce into intricate, interconnecting fibrilar networks with micron thickness dimensions.

It is noted that only a limited number of microencapsulation techniques can produce particles smaller than 10 microns, and those techniques are associated with significant losses of polymer, the material to be encapsulated, or both. This is particularly problematic where the active agent is a gene under the control of a promoter, which large DNA molecules are particularly labile to manufacturing processes and are extremely expensive to produce. The present invention provides a method to produce nano to micro-sized particles with minimal losses. The described methods can result in product yields greater than 80%.

The methods of the invention also can produce microparticles characterized by a homogeneous size distribution. Typical microencapsulation techniques produce heterogeneous size distributions ranging from 10 μm to mm sizes. Prior art methodologies attempt to control particle size by parameters such as stirring rate, temperature, polymer/suspension bath ratio, etc. Such parameters, however, have not resulted in a significant narrowing of size distribution. The present invention can produce, for example, nanometer sized particles which are relatively monodisperse in size. By producing a microparticle that has a well defined and less variable size, the properties of the microparticle such as when used for release of a bioactive agent can be better controlled. Thus, the invention permits improvements in the preparation of sustained release formulations for administration to subjects.

As mentioned above, the methods of the invention can be, in many cases, carried out in less than five minutes in the entirety. It is typical that preparation time may take anywhere from one minute to several hours, depending on the solubility of the polymer and the chosen solvent, whether the agent will be dissolved or dispersed in the solvent and so on. Nonetheless, the actual encapsulation time typically is less than thirty seconds.

After formation of the microcapsules, they are collected by centrifugation, filtration, and the like. Filtering and drying may take several minutes to an hour depending on the quantity of material encapsulated and the methods used for drying the nonsolvent. The process in its entirety may be discontinuous or a continuous process.

Because the process does not require forming the solvent into an emulsion, it generally speaking may be regarded as a more gentle process than those that require emulsification. As a result, materials such as whole plasmids including genes under the control of promoters can be encapsulated without destruction of the DNA as a result of the emulsification process. Thus the invention particularly contemplates encapsulating oligonucleotides such as plasmids, vectors, external guide sequences for RNAase P, ribozymes and other sensitive oligonucleotides, the structure and function of which could be adversely affected by aggressive emulsification conditions and other parameters typical of certain of the prior art processes. Delivery of antisense, of course, also is possible according to this invention.

Included in Table I below are examples of a variety of polymers, solvents, viscosities, nonsolvents, and concentrations tested in the phase inversion process used for manufacturing microparticles.

TABLE 1

| Polymer | MW | Concentration | Viscosity | Solvent | Non-Solvent | Drug | Concentration | Product |
|---|---|---|---|---|---|---|---|---|
| polystyrene | 2 K | 5% | | MeCl$_2$ | pet ether | rhodamine | 0.1% | |
| polystyrene | 2 K | 10% | | MeCl$_2$ | pet ether | rhodamine | 0.1% | |
| polystyrene | 50 K | 1% | | MeCl$_2$ | pet ether | none | — | |
| polystyrene | 50 K | 1% | | MeCl$_2$ | pet ether | rhodamine | 0.1% | 1–5 μm |
| polystyrene | 50 K | 3% | | MeCl$_2$ | pet ether | rhodamine | 0.1% | |
| polystyrene | 50 K | 5% | | MeCl$_2$ | pet ether | rhodamine | 0.1% | 500 nm–2 μm |
| polystyrene | 50 K | 10% | | MeCl$_2$ | pet ether | rhodamine | 0.1% | 1–4 μm |
| polystyrene | 50 K | 15% | | MeCl$_2$ | pet ether | rhodamine | 0.1% | 1–10 μm & aggr |
| polystyrene | 50 K | 20% | | MeCl$_2$ | pet ether | rhodamine | 0.1% | large aggregate |
| polystyrene | 50 K | 1% | | MeCl$_2$ | ethanol | rhodamine | 0.1% | |
| polystyrene | 50 K | 5% | | MeCl$_2$ | ethanol | rhodamine | 0.1% | <100 nm |
| polystyrene | 50 K | 10% | | MeCl$_2$ | ethanol | rhodamine | 0.1% | <100 nm–3 μm |
| polycaprolactone | 72 K | 1% | 3.188 | MeCl$_2$ | pet ether | rhodamine | 0.1% | 11–3 μm |
| polycaprolactone | 72 K | 5% | 7.634 | MeCl$_2$ | pet ether | rhodamine | 0.1% | 1–3 μm large aggr |
| polycaprolactone | 112 K | 1% | 4.344 | MeCl$_2$ | pet ether | rhodamine | 0.1% | 500 nm–5 μm |
| polycaprolactone | 112 K | 5% | | MeCl$_2$ | ethanol | rhodamine | 0.1% | Large aggregate |
| polyvinylphenol | 1.5–7 K | 1% | | acetone | pet ether | none | — | 250 nm–1 μm |
| polyvinylphenol | 1.5–7 K | 5% | | acetone | pet ether | none | — | |
| polyvinylphenol | 1.5–7 K | 10% | " | acetone | pet ether | none | — | |
| polyvinylphenol | 9–11 K | 1% | | acetone | pet ether | none | — | 100 nm–2 μm |
| polyvinylphenol | 9–11 K | 5% | | acetone | pet ether | none | — | 250 nm–2.5 μm |
| polyvinylphenol | 9–11 K | 10% | | acetone | pet ether | none | — | 500 nm–10 μm |
| polylactic acid | 2 K | 1% | 0.876 | MeCl$_2$ | pet ether | rhodamine | 0.1% | 100 nm |
| polylactic acid | 2 K | 5% | 1.143 | MeCl$_2$ | pet ether | rhodamine | 0.1% | 500 nm–2 μm |
| polylactic acid | 2 K | 10% | 2.299 | MeCl$_2$ | pet ether | rhodamine | 0.1% | 1–10 μm brittle |
| polylactic acid | 24 K | 1% | 1.765 | MeCl$_2$ | pet ether | rhodamine | 0.1% | 100 nm |
| polylactic acid | 24 K | 5% | 2.654 | MeCl$_2$ | pet ether | rhodamine | 0.1% | 500 nm–1 μm |
| polylactic acid | 24 K | 10% | 3.722 | MeCl$_2$ | pet ether | rhodamine | 0.1% | 10 μm aggr |
| polylactic acid | 40–100 K | 1% | 2.299 | MeCl$_2$ | pet ether | rhodamine | 0.1% | |
| polylactic acid | 40–100 K | 5% | 2.832 | MeCl$_2$ | pet ether | rhodamine | 0.1% | |
| polylactic acid | 40–100 K | 10% | 6.122 | MeCl$_2$ | pet ether | rhodamine | 0.1% | |
| polylactic acid | 100 K | 1% | 2.566 | MeCl$_2$ | pet ether | rhodamine | 0.1% | 100 nm |
| poly-lactic acid | 100 K | 5% | 4.433 | MeCl$_2$ | pet ether | rhodamine | 0.1% | 500 nm–2 μm aggr |
| poly-lactic acid | 100 K | 10% | 8.256 | MeCl$_2$ | pet ether | rhodamine | 0.1% | film/aggr |
| ethylene-vinyl acetate | 55 K | 1% | | MeCl$_2$ | pet ether | rhodamine | 0.1% | Globular strands |
| ethylene-vinyl acetate | 55 K | 5% | | MeCl$_2$ | pet ether | rhodamine | 0.1% | coalesced strands |
| ethylene-vinyl acetate | 55 K | 10% | | MeCl$_2$ | pet ether | rhodamine | 0.1% | continuous sheet |

TABLE 1-continued

| Polymer | MW | Concentration | Viscosity | Solvent | Non-Solvent | Drug | Concentration | Product |
|---|---|---|---|---|---|---|---|---|
| PAN/PVC | | 1% | 2.566 | acetone | pet ether | none | — | coarse 1–20 μm |
| PAN/PVC | | 5% | 15.903 | acetone | pet ether | none | — | 100 μm aggr |

It will be understood by those of ordinary skill in the art that the microparticles can be formed by other processes such as by certain spray drying technologies. Spray drying is typically a process for preparing 1–10 micron sized microspheres in which the core material to be encapsulated is dispersed or dissolved in the polymer solution (typically aqueous). The solution or dispersion is pumped through a micronizing nozzle driven by a flow of compressed gas, and the resulting aerosol is suspended in a heated cyclone of air, allowing the solvent to evaporate from the microdroplets. The solidified particles pass into a second chamber and are trapped in a collection flask.

Numerous polymers can be used to prepare DNA containing microparticles. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone.

Examples of preferred non-biodegradable polymers include ethylene vinyl acetate, poly(meth)acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginnate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as a co-polymer. The most preferred polymers are polyesters, polyanhydrides, polystyrenes and blends thereof.

Particularly preferred are bioadhesive polymers. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups. Numerous bioadhesive polymers are discussed in that application. Representative bioadhesive polymers of particular interest include bioerodible hydrogels described by H. S. Sawhney, C. P. Pathak and J. A. Hubell in *Macromolecules* 1993, 26:581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butyl methacrylate), poly(isobutyl methacrylate), poly(hexl methacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate). Most preferred is poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers may be combined with metal oxide particles to improve bioadhesion even more than with the organic additives alone. Organic dyes because of their electronic charge and hydrophobicity/hydrophilicity can either increase or;decrease the bioadhesive properties of polymers when incorporated into the polymers. The incorporation of oligomer compounds into a wide range of different polymers which are not normally bioadhesive dramatically increases their adherence to tissue surfaces such as mucosal membranes.

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 daltons, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile.. As analyzed by gel permeation chromatography, the molecular weight may be, for example, on the order of 200–400 for fumaric acid oligomer (FAPP) and 2000–4000 for sebacic acid oligomer (SAPP). The anhydride bonds can be detected by Fourier transform infrared spectroscopy by the characteristic double peak at 1750 $cm^{-1}$ and 1820 $cm^{-1}$, with a corresponding disappearance of the carboxylic acid peak normally at 1700 $cm^{-1}$.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic dyes, because of their electronic charge and hydrophilicity/hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2,3, 13 and 86, rose bengal, safranin o, Sudan III and IV, Sudan black B and toluidine blue.

The bioadhesive properties of a polymer are enhanced by incorporating a metal compound into the polymer to enhance the ability of the polymer to adhere to a tissue surface such as a mucosal membrane. Metal compounds which enhance the bioadhesive properties of a polymer preferably are water-insoluble metal compounds, such as water-insoluble metal oxides and hydroxides. The metal compounds can be incorporated within a wide range of hydrophilic and hydrophobic polymers including proteins, polysaccharides and synthetic biocompatible polymers. As defined herein, a water-insoluble metal compound is defined as a metal compound with little or no solubility in water, for example, less than about 0.0–0.9 mg/ml.

The water-insoluble metal compounds, such as metal oxides, can be incorporated by one of the following mechanisms: (a) physical mixtures which result in entrapment of the metal compound; (b) ionic interaction between metal compound and polymer; (c) surface modification of the polymers which would result in exposed metal compound on the surface; and (d) coating techniques such as fluidized bead, pan coating or any similar methods known to those skilled in the art, which produce a metal compound enriched layer on the surface of the device.

Preferred properties defining the metal compound include: (a) substantial insolubility in aqueous environments, such as acidic or basic aqueous environments (such as those present in the gastric lumen); and (b) ionizable surface charge at the pH of the aqueous environment.

The water-insoluble metal compounds can be derived from metals including calcium, iron, copper, zinc, cadmium, zirconium and titanium. For example, a variety of water-insoluble metal oxide powders may be used to improve the bioadhesive properties of polymers such as ferric oxide, zinc oxide, titanium oxide, copper oxide, barium hydroxide, stannic oxide, aluminum oxide, nickel oxide, zirconium oxide and cadmium oxide. The incorporation of water-insoluble metal compounds such as ferric oxide, copper oxide and zinc oxide can tremendously improve adhesion of the polymer to tissue surfaces such as mucosal membranes, for example in the gastrointestinal system. The polymers incorporating a metal compound thus can be used to form or coat drug delivery devices to improve their bioadhesive properties.

In one embodiment, the metal compound is provided as a fine particulate dispersion of a water-insoluble metal oxide which is incorporated throughout the polymer or at least on the surface of the polymer which is to be adhered to a tissue surface. For example, in one embodiment, water-insoluble metal oxide particles are incorporated into a polymer defining or coating a microparticle. In a preferred embodiment, the metal oxide is present as a fine particulate dispersion on the surface of the microparticle.

The fine metal oxide particles can be produced for example by micronizing a metal oxide by mortar and pestle treatment to produce particles ranging in size, for example from 10.0–300 nm. The metal oxide particles can be incorporated into the polymer, for example, by dissolving or dispersing the particles into a solution or dispersion of the polymer prior to microparticle formation, and then can be incorporated into the polymer during microparticle formation using a procedure for forming microparticle such as one of those described herein. The incorporation of metal oxide particles on the surface of the microparticle advantageously enhances the ability of the of the microsphere to bind to mucosal membranes or other tissue surfaces and improves the drug delivery properties of the microparticle.

While not being limited to any theory, it is possible that the enhanced binding of the polymers incorporating a metal compound is due to the presence of partially ionized metal compounds, such as divalent or trivalent cations, on the surface of the polymer which interact, for example, via an ionic binding attraction with negatively charged glycosubstances such as sialic acid and L-fucose groups on the mucosal membrane surface. Multivalent ions such as divalent or trivalent cations in the metal compounds generally have the strongest affinity for the negatively-charged mucin chains.

As used herein, a "gene" is an isolated nucleic acid molecule of greater than thirty nucleotides, more typically one hundred nucleotides or more, in length. It generally will be under the control of an appropriate promoter, which may be inducible, repressible, or constitutive. Any genes that would be useful in replacing or supplementing a desired function, or achieving a desired effect such as the inhibition of tumor growth, could be introduced using the microparticles described herein. Promoters can be general promoters, yielding expression in a variety of mammalian cells, or cell specific, or even nuclear versus cytoplasmic specific. These are known to those skilled in the art and can be constructed using standard molecular biology protocols.

A list of genes that have been approved for gene therapy by RAC between the years of 1990 and 1994 is provided in Table 2.

TABLE 2

Human Gene Therapy Protocols Approved by RAC: 1990–1994

| | | |
|---|---|---|
| Severe combined immune deficiency (SCID) due to adenosine deaminase (ADA) deficiency | Autologous lymphocytes transduced with human ADA gene | Jul. 31, 1990 |
| Advanced cancer | Tumor-infiltrating lymphocytes transduced with tumor necrosis factor gene | Jul. 31, 1990 |
| Advanced cancer | Immunization with autologous cancer cells transduced with tumor necrosis factor gene | Oct. 07, 1991 |
| Advanced cancer | Immunization with autologous cancer cells transduced with interleukin-2 gene | Oct. 07, 1991 |
| Familial hypercholesterolemia | Ex vivo gene therapy | Oct. 08, 1991 |
| Malignancy | In vivo gene transfer into tumors | Feb. 10, 1992 |
| Cancer | Gene transfer | Feb. 10, 1992 |
| Relapsed/refractory neuroblastoma | Cytokine-gene modified autologous neuroblastoma cells (Phase I study) | Jun. 01, 1992 |
| Brain tumors | Intratumoral transduction with thymidine kinase gene and intravenous ganciclovir | Jun. 01, 1992 |
| Metastatic melanoma | Immunization with HLA-A2 matched allogeneic melanoma cells that secrete interleukin-2 | Jun. 02, 1992 |
| Advanced renal cell carcinoma | Immunization with interleukin-2 secreting allogeneic HLA-A2 matched renal-cell carcinoma cells | Jun. 02, 1992 |
| Cancer | Interleukin-4-gene modified antitumor vaccine (pilot study) | Sep. 15, 1992 |
| Cystic fibrosis | Replication deficient recombinant adenovirus carrying cDNA of normal human cystic fibrosis transmembrane conductance regulator (CFRT) gene; single administration to the lung (Phase I study) | Dec. 03, 1992 |
| Cystic fibrosis | E1-deleted adenovirus vector for delivering CFTR gene (Phase I study) | Dec. 03, 1992 |
| Cystic fibrosis | Adenovirus vector used for delivering CFTR gene to nasal epithelium | Dec. 04, 1992 |
| Recurrent glioblastoma (brain tumor) | In vivo tumor transduction using herpes simplex thymidine kinase gene/ganciclovir system | Mar. 01, 1993 |
| Metastatic renal cell carcinoma | Injection of non-replicating autologous tumor cells prepared +/− granulocyte-macrophage colony stimulating factor transduction (Phase I study) | Mar. 01, 1993 |

TABLE 2-continued

Human Gene Therapy Protocols Approved by RAC: 1990–1994

| | | |
|---|---|---|
| Cystic fibrosis | Use of replication deficient recombinant adenovirus vector to deliver human CFTR cDNA to the lungs (Phase I study) | Mar. 02, 1993 |
| Cystic fibrosis | Use of E1-deleted adenovirus for delivery of CFTR gene to nasal cavity (Phase I study) | Mar. 02, 1993 |
| Disseminated malignant melanoma | Human gamma-interferon transduced autologous tumor cells (Phase I study) | Jun. 07, 1993 |
| Ovarian cancer | Use of modified retro viruses to introduce chemotherapy resistance sequences into normal hematopoietic cells for chemoprotection (pilot study) | Jun. 07, 1993 |
| Cancer | Immunotherapy by direct gene transfer into tumors | Jun. 07, 1993 |
| Gaucher's disease | Ex vivo gene transfer and autologous transplantation of CD34 + cells | Jun. 07, 1993 |
| Gaucher's disease | Retro viral-mediated transfer of cDNA for human glucocerebrosidase into hematopoietic stem cells | Jun. 07, 1993 |
| Asymptomatic patients infected with HIV-1 | Murine Retro viral vector encoding HIV-1 genes [HIV-IT(V)] | Jun. 07, 1993 |
| AIDS | Effects of a transdominant form of rev gene on AIDS intervention | Jun. 07, 1993 |
| Recurrent pediatric malignant astrocytomas | In vivo tumor transduction with herpes simplex thymidine kinase gene | Jun. 08, 1993 |
| Advanced cancer | Human multiple-drug resistance (MDR) gene transfer | Jun. 08, 1993 |
| Brain tumors | Episome-based antisense cDNA transcription of insulin-like growth factor I | Jun. 08, 1993 |
| Small-cell lung cancer | Cancer cells transfected with and expressing interleukin-2 gene (Phase I study) | Sep. 09, 1993 |
| Breast cancer (Post-chemotherapy) | Retro viral mediated transfer of the human MDR gene into hematopoietic stem cells (autologous transplantation) | Sep. 09, 1993 |
| Recurrent pediatric brain tumors | Intra-tumoral transduction with thymidine kinase gene and intravenous administration of ganciclovir | Sep. 09, 1993 |
| Malignant melanoma | Immunization with interleukin-2 secreting allogeneic human melanoma cells | Sep. 10, 1993 |
| HIV infection | Autologous lymphocytes transduced with catalytic ribozyme that cleaves HIV-1 RNA (Phase I study) | Sep. 10, 1993 |
| Metastatic melanoma | Genetically engineered autologous tumor vaccines producing interleukin-2 | Sep. 10, 1993 |
| Leptomeningeal carcinomatosis | Intrathecal gene therapy | Dec. 02, 1993 |
| Colon carcinoma | Injection with autologous irradiated tumor cells and fibroblasts genetically modified to secrete interleukin-2 | Dec. 2, 1993 |
| Gaucher's disease | Retro virus-mediated transfer of cDNA for human glucocerebrosidase into peripheral blood repopulating patients' cells | Dec. 3, 1993 |
| HIV infection | Murine Retro viral vector encoding HIV-IT(V) genes (open label Phase I/II trial) | Dec. 03, 1993 |

TABLE 2-continued

Human Gene Therapy Protocols Approved by RAC: 1990–1994

| | | |
|---|---|---|
| Advanced (stage IV) melanoma | Induction of cell-mediated immunity against tumor-associated antigens by B7-transfected lethally irradiated allogeneic melanoma cell lines (Phase I study) | Dec. 03, 1993 |
| Advanced colorectal carcinoma | Immunotherapy by direct gene transfer into hepatic metastases (Phase I study) | Dec. 03, 1993 |
| Melanoma | Adoptive immunotherapy with activated lymph node cells primed in vivo with autologous tumor cells transduced with interleukin-4 gene | Dec. 03, 1993 |
| Cystic fibrosis | Cationic liposome-mediated transfer of CFTR gene into nasal airway (Phase I study) | Dec. 03, 1993 |
| Cystic fibrosis | Adenovirus-mediated transfer of CFTR gene to the nasal epithelium and maxillary sinus | Dec. 03, 1993 |
| Pediatric neuroblastoma | Immunization with gamma-interferon transduced neuro blastoma cells (ex vivo) (Phase I) | Mar. 03, 1994 |
| HIV infection (identical twins) | Adoptive transfer of syngeneic Cytotoxic T lymphocytes (Phase I/II pilot study) | Mar. 03, 1994 |
| Emphysema | Expression of an exogenously administered human alpha-I-antitrypsin gene in respiratory tract | Mar. 03, 1994 |
| Metastatic renal cell carcinoma | Immunotherapy by direct gene transfer into metastatic lesions (Phase I study) | Mar. 04, 1994 |
| Malignant melanoma | Immunotherapy by direct gene transfer (Phase I study) | Mar. 04, 1994 |
| Non-small cell lung cancer | Modification of oncogene and tumor suppressor gene expression (first antisense therapy; original protocol approved by RAC Sep. 15, 1992, but then approval withdrawn Dec. 03, 1993) | Mar. 04, 1994 (resubmitted protocol) |
| Metastatic colorectal cancer | Polynucleotide augmented anti-tumor immunization to human carcinoembryonic antigen (Phase I) | Jun. 09, 1994 |
| Rheumatoid arthritis | Transduction_interleukin-1 receptor antagonist gene to human joints | Jun. 09, 1994 |
| Breast cancer (chemo-protection during therapy) | Use of modified Retro virus to introduce chemotherapy resistance sequences into normal hematopoietic cells (pilot study) | Jun. 09, 1994 |
| Fanconi's anemia | Retro viral mediated gene transfer of the Fanconi anemia complementation group C gene to hematopoietic progenitors | Jun. 09, 1994 |
| Non-small cell lung cancer | Modification of tumor suppressor gene expression and induction of apoptosis with adenovirus vector expressing wild type p53 and cisplatin | Jun. 10, 1994 |
| Glioblastoma | Injection of tumor cells genetically modified to secrete interleukin-2 (Phase I study) | Jun. 10, 1994 |
| Cancer | Direct injection of tumors with autologous fibroblasts engineered to contain interleukin-12 gene | Jun. 10, 1994 |
| Metastatic prostate carcinoma | Autologous human granulocyte macrophage-colony stimulating factor gene transduced prostate cancer vaccine *(first protocol to be approved under the accelerated review process; ORDA = Office of Recombinate DNA Activities) | ORDA/NIH Aug. 03, 1994* |
| Cystic fibrosis (adults with mild disease) | Adeno-associated virus vector to deliver CFTR gene to cells in nose and lung (Phase I study) | Sep. 12, 1994 |
| Metastatic breast cancer | In vivo infection with breast-targeted Retro viral vector expressing antisense c-fox or antisense c-myc RNA | Sep. 12, 1994 |
| Cystic fibrosis | Repeat administration of replication deficient recombinant adenovirus containing normal CFTR cDNA to patient's airways | Sep. 12, 1994 |
| Metastatic breast cancer (refractory or recurrent) | Non-viral system (liposome-based) for delivering human interleukin-2 gene into autologous tumor cells (pilot study) | Sep. 12, 1994 |
| Mild Hunter syndrome (muco-polysaccharidosis type II) | Retro viral-mediated transfer of the iduronate-2-sulfatase gene into lymphocytes | Sep. 13, 1994 |
| Peripheral artery disease | Arterial gene transfer for therapeutic angiogenesis | Sep. 13, 1994 |
| Advanced CNS malignancy | Use of recombinant adeno-virus (Phase I study) | Sep. 13, 1994 |
| Advanced mesothelioma | Use of recombinant adeno-virus (Phase I study) | Sep. 13, 1994 |

The foregoing represent only examples of genes that can be delivered according to the methods of the invention. Suitable promoters, enhancers, vectors, etc., for such genes are published in the literature associated with the foregoing trials. In general, useful genes replace or supplement function, including genes encoding missing enzymes such as adenosine deaminase (ADA) which has been used in clinical trials to treat ADA deficiency and cofactors such as insulin and coagulation factor VIII. Genes which affect regulation can also be administered, alone or in combination with a gene supplementing or replacing a specific function. For example, a gene encoding a protein which suppresses expression of a particular protein-encoding gene can be administered by the microparticles of the invention. Because the mucosal epithelium is rich in immune-system cells, the invention is particularly useful in delivering genes which stimulate the immune response, including genes encoding viral antigens, tumor antigens, cytokines (e.g. tumor necrosis factor) and inducers of cytokines (e.g. endotoxin). Because the mucosal epithelium is a route to systemic circulation, the invention can be used to deliver genes encoding various pharmacological agents. These genes may transfect cells locally within the mucosal epithelium for release of the gene product to systemic circulation, or the genes may transfect cells remote from the mucosal epithelium, being delivered to the remote location, for example, via systemic circulation of the microparticles.

Genes can be obtained or derived from a variety of sources, including literature references, Genbank, or commercial suppliers. They can be synthesized using solid phase synthesis if relatively small, obtained from deposited samples such as those deposited with the American Type Culture Collection, Rockville, Md. or isolated de novo using published sequence information.

The genes described herein are distinguished from short oligonucleotides such as antisense and ribozymes by their length and function. Unlike such short oligonucleotides, genes encode protein and therefore will typically be a minimum of greater than 100 base pairs in length, more typically in the hundreds of base pairs. It was not predictable that these long nucleic acid sequences, highly susceptible to breakage and distortion of secondary and tertiary sequence, could be incorporated into microparticles without damage, and not predictable that the encapsulated DNA would survive the environment of the stomach and be delivered and released intracellularly in active form for transfection cells.

As used herein, vectors are agents that transport the gene into a cell without degradation and include a promoter yielding expression of the gene in the cells into which it is delivered. Vectors are divided into two classes:

A) Biological agents derived from viral, bacterial or other sources.

B) Chemical/physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells.

Retroviral vectors are the vectors most commonly used in clinical trials, since they carry a larger genetic payload than other viral vectors. However, they are not useful in non-proliferating cells.

Adenovirus vectors are relatively stable and easy to work with, have high titers, and can be delivered in aerosol formulation. However, many people may have pre-existing antibodies negating effectiveness and they are difficult to produce in quantity.

Pox viral vectors are large and have several sites for inserting genes, they are thermostable and can be stored at room temperature. However, they cannot be transmitted from host to host and there are some safety issues since they can enter other cells.

Plasmids are double stranded DNA which may exist in supercoiled, linear, open circular or denatured conformation. Plasmids used for gene transfer typically contain the gene of interest, a promoter/enhancer, a poly (A) termination sequence, an origin of replacation, intron and/or a reporter gene. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells may substantially increase the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. The chemical/physical methods have a number of problems, however, and will typically not be used with the microparticles described herein. For example, chemicals mediators are impractical for in vivo use: when calcium phosphate is used there appears to be very low transduction rate, when sodium butyrate is used the inserted gene is highly unstable and when glycerol is used inserted gene is rapidly lost.

It is possible to incorporate nucleic acid molecules into liposomes or complexed to liposomes which are then incorporated into the microparticles for delivery to cells. The ratio of liposome to polymer solution is important in determining whether the liposomes will remain as separate entities during the process for incorporation into the microparticles. If the ratio of solvent is too high, the phospholipid will dissolve into the polymer solvent, rather than remaining as part of the liposome bilayer. This is a function of the liposome composition, polymer concentration, and solvent composition. The liposomes can increase the efficiency of the transfer of the DNA into the cells when the liposomes are released from the microparticles. Liposomes are commercially available from Gibco BRL, for example, as LIPO-FECTIN® and LIPOFECTACE®, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

TABLE 2

Summary of various the Vectors Currently Used in Gene Therapy

| | Size Constraints | Specificity of Targeting | Immunogenicity/ Toxicity | Sustained/High/Low/ Controlled Expression |
|---|---|---|---|---|
| Retrovirus | 7 Kb | none | none | low, uncontrolled transient transfection |
| Adenovirus | 7 Kb | none | high immunogenicity | low, uncontrolled transient transfection |
| Liposome | none | none | toxic at high doses | low, uncontrolled transient transfection |

The methods of the invention are applied to subjects. As used herein, subjects means humans, nonhuman primates, horses, goats, cows, sheep, pigs, dogs, cats and rodents.

When used therapeutically, the compounds of the invention are administered in therapeutically effective amounts. In general, a therapeutically effective amount means that amount necessary to delay the onset of, inhibit the progression of, ameliorate the symptoms of or halt altogether the particular condition being treated. It is less than that amount that produces medically unacceptable side-effects. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.0001 mg/kg (active agent/body weight) to about 1000 mg/kg, preferably from about 0.1 mg/kg to about 20 mg/kg in one or more dose administrations daily, for one or more days.

The therapeutics of the invention can be administered by any conventional route. The preferred route is to the mucosal epithelium, such as with an oral formulation, aerosol for respiratory tract delivery, vaginal formulation, rectal formulation, nasal formulation, buccal formulation or occular formulation. The administration can, however, be, via any conventional route, including intramuscular, intracavity, subcutaneous, or transdermal administration. Techniques for preparing aerosol delivery systems are well known to those of skill in the art. Generally, such systems should utilize components which will not significantly impair the biological properties of the therapeutic (see, for example, Sciarra and Cutie, "Aerosols," in *Remington's Pharmaceutical Sciences,* 18th edition, 1990, pp 1694–1712; incorporated by reference). The PIN process for making the microparticles of the invention is particularly suited to making aerosols. Those of skill in the art can readily determine the various parameters and conditions for producing aerosols or other formulations without resort to undue experimentation.

Oral formulations are well known to those skilled in the art, and include tablets, capsules, or liquids with flavorants, stabilizers and the like. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The pharmaceutical preparation of microparticles may be used alone or in combination with a therapeutic agent for treating the disease or condition for which the microparticles are being administered. Known therapeutics are described in medical textbooks such as Harrisons, Principles of Internal Medicine (McGraw Hill, Inc., N.Y.). The particular therapeutic used depends on the nature of the disease or condition being treated.

In some embodiments, a common administration vehicle (e.g., pill, tablet, implant, injectable solution, etc.) would contain both the microparticles useful in this invention and the therapeutic agent for treating the disease or condition. Thus, the present invention also provides pharmaceutical compositions, for medical use, which comprise the microparticles of the invention together with one or more pharmaceutically acceptable carriers thereof and optionally other therapeutic ingredients.

The pharmaceutical compositions should contain a therapeutically effective amount of the microparticles in a unit of weight or volume suitable for administration to a patient. The term "pharmaceutically acceptable" means a non-toxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials which are well known in the art.

The methods and products of the invention permit the noninvasive delivery of genes under the control of promoters for transfection of cells in vivo. The materials of the invention can be applied to epithelial surfaces, including mucosal epithelium. As will be seen from the examples below, both epithelial and nonepithelial cells can be transformed. In the oral delivery methods of the invention, for example, adsorptive and nonadsorptive intestinal epithelial cells can be transfected, as well as gut associated lymphoid tissue and liver cells.

EXAMPLES

Example 1

Microspheres Produced by Phase Inversion Encapsulation Exhibit Enhanced Bioavailability of Encapsulated Drugs In Vivo 1. Oral Delivery of Microparticles Studies were conducted to determine the fate of orally administered P(FA:SA)20:80 microparticles. The microparticles contained rhodamine and had a particle size range of between 0.1 and 1.0 micrometers. Rats were fed a single dose of 3 mg of such microparticles. As early as one hour posted-feeding of a single dose, microparticles were observed to traverse the mucosal epithelium by passing between absorptive cells (paracellular route). In addition, microparticles were seen crossing through follicle associated epithelium (FAE) and into the Peyer's patches. After three and six hours, an even greater number of microparticles were seen between epithelial cells and in the Peyer's patches. Focal areas demonstrated massive amounts of non-selective uptake, by both absorptive cells and Peyer's patches. Liver samples showed large numbers of nanospheres with apparently normal looking hepatocytes. Spleen sections also showed nanospheres, but fewer than in the liver. At twelve hours, large numbers spheres were still observed in between villous epithelial cells and in the Peyer's patches. Similar sections were observed even at twenty-four hours post-feeding.

This experiment showed extensive uptake of microparticles extending over at least twenty-four hours, following a single oral dose. Microparticles apparently crossed the epithelial boundary by passing in between cells. The observed uptake did not seem to be limited to the FAE overlying the Peyer's patches; uptake occurred diffusely by absorptive epithelium as well as FAE.

Transmission electron microscopy experiments using electron-opaque tracers such as micronized ferric oxide or 5 nm colloidal gold that had been microencapsulated with bioadhesive P(FASA) 20:80 were also conducted. The findings demonstrated that nanospheres in great number were indeed being taken up by absorptive epithelial cells lining the small intestine. In a typical thin section of an absorptive cell, up to one hundred nanospheres could be counted. While the results of light microscopy indicated a paracellular means of entry, these electron micrographs showed many microparticles within cells. The mechanism of entry is not known although several particles were occasionally observed in clear "endocytotic" vesicles located directly beneath the terminal web region in proximity to the apical microvillous border. The range of particle sizes observed in the cytoplasm of cells was 40–120 nm, well below the resolution of normal light optics and therefore undetectable by light microscopy. Nanoparticles were visualized in the cytoplasm, inside membranous profiles of the endoplasmic reticulum and Golgi apparatus and generally in the supranuclear (apical) portion of the absorptive cell. Occasionally, nanoparticles were seen near the basal aspects of the cell. Spheres were often found near the lateral borders of the cell, in the intracellular spaces and in close apposition to the tight junctions. These findings suggest that translocation of nanospheres via the transcellular route occurred in addition to paracellular movement.

2. Oral Delivery of Insulin

Insulin was encapsulated in P(FA)-PLGA(50:50) polymer blends using the phase inversion nanoencapsulation methods. After measuring fasting blood glucose levels, fasted rats were injected subcutaneously with an initial glucose load and then fed either a suspension of nanospheres containing 20 IU zinc-insulin (micronized FeO was included an electron dense tracer) in saline or else sham fed saline only. Blood glucose levels (BGL) were assayed at intervals after feeding.

The controls showed the expected response to the glucose load. BGL rose by 40 mg/dL after three hours and then slowly started to return towards baseline. In contrast, animals fed the encapsulated insulin formulation had consistently lower blood glucose levels than the control animals at three of the four time points that were sampled. After 1.5 hours, the BGL was 20 mg/dL below baseline compared to 30 mg/dL above baseline for control animals. At three hours the BGL of the nanoparticle treated animals rose to 20 mg/dL above baseline compared to a 40 mg/dL rise for the control animals (not statically different). At four hours, the BGL of the nanoparticle-fed animals was nearly 30 mg/dL below baseline, compared to a BGL of 20 mg/dL above base line for the control animals. After five hours, the glucose levels of the test group were lower than at four hours, while the levels of the control animals were still 35 mg/dL above baseline. Because the animals fed the encapsulated insulin preparation were better able to regulate the glucose load, it is clear that the insulin was not harmed by the encapsulation method, that the insulin survived the environment of the stomach, the insulin crossed the intestinal barrier and the insulin was released from the nanoparticles in a bioactive form. A widespread distribution of insulin-loaded nanospheres also was observed. The spheres were observed in great numbers, traversing the mucosal epithelium in the small intestine, in the Peyer's patches, in the lamina propria, in the lacteals and in the blood vessels of the gut wall. Nanoparticles also were observed in spleen and other tissue samples. Thus, systemic delivery of both insulin and nanoparticles was demonstrated.

3. Encapsulation and Oral Deliver of Dicumarol

Dicumarol containing microspheres were produced as described above in Example 2, subsection 1. Equal doses of dicumarol, spray dried dicumarol and polyanhydride (FA:SA) 20:80 encapsulated dicumarol (25 mg drug/kg body weight) suspended in 1.5 ml maple syrup were fed to catheterized rats (250–350 g). Blood samples were taken at regular intervals and serum was assayed for dicumarol concentrations using a UV spectrophotometric method.

The results of the in vivo studies indicate that the polyanhydride (FA:SA) microcapsule formulation had significantly increased bioavailability compared to the unencapsulated formulations, including the micronized drug. At 12 hours post-feeding, the serum concentrations for the polyanhydride (FA:SA) formulations were significantly higher than for the controls. At 48 hours post-feeding, the serum levels of dicumarol in the controls had returned to baseline, while those animals fed the bioadhesive polyanhydride formulation had detectable drug concentrations for at least 72 hours.

TABLE 1

ORAL BIOAVAILABILITY OF DICUMAROL

|  | STOCK DICUMAROL CONTROL | SPRAY DICUMAROL CONTROL | P(FA:SA) 20:80 "PIN" ENCAPSULATED DICUMAROL |
|---|---|---|---|
| C MAX (ug/ml) | 11.53 ± 1.10* | 17.94 ± 1.22 | 18.63 ± 1.76* |
| T MAX (hrs) | 9.87 ± 1.76 | 9.42 ± 1.36 | 10.61 ± 0.02 |
| t½ (half life) (hrs) | 18.25 ± 3.30 | 16.21 ± 0.87 | 17.92 ± 0.41 |
| AUC (area under curve) (ug/ml - hrs) | 171.48 ± 33.16 | 232.10 ± 19.20≠ | 363.59 ± 70.95≠ |

*= Significantly different at p < .03
≠= Significantly different at p < .005
(means ± std error)

These results indicate that phase inversion encapsulation of drugs in bioadhesive formulations, such as the polyanhydride (FA:SA) can increase bioavailability.

Example 2

Incorporation of DNA Into Polymeric Nanospheres by Phase Inversion

This example provides a description of the incorporation of plasmid DNA into poly(fumaric acid:sebacic acid) 20:80 (P(FA:SA)) using a phase inversion technique.

Materials

P(FA:SA) 20:80 (synthesized by a method of A. Domb & R. Langer, Journal of Polymer Science, 1987, v.25, p.3373–3386), a reporter plasmid pCMV/βgal (Clonetech), methylene chloride (Fisher) and petroleum ether (Fisher) were used to construct the nanospheres.

Methods 200 mg of P(FA:SA) in methylene chloride (1% wt/vol) is vortexed (30 sec) with 2 mg of pCMV/βgal in distilled water (1 mg/ml), frozen in liquid nitrogen and lyophilized overnight to disperse the DNA in the polymer. The purpose of this step was to reduce the particulate size and prevent aggregation of the DNA. DNA present in the disperse phase of the emulsion would not be able to aggregate due to the physical separation induced by the continuous polymer phase. The resulting mixture was redissolved in 2 ml of methylene chloride, poured into 200 ml of petroleum ether and filtered to recover microspheres encapsulating the DNA.

Results

Polymer nanoparticles produced using this technique were analyzed to determine whether DNA was encapsulated within the nanoparticles. Plasmid DNA was extracted from the nanoparticles and subjected to agarose gel electrophoresis. The results indicate that DNA was encapsulated without degradation. Thus, the phase inversion technique can be used to incorporate very large intact molecular weight plasmid DNA ($7.2 \times 10^6$ Daltons) in biodegradable nanoparticles.

Example 3

Release of pCMV/βgal from P(FA:SA) Nanoparticles

This in vitro example demonstrates that plasmid DNA can be released-from P(FA:SA) nanoparticles.

Materials

P(FA:SA)-pCMV/βgal nanoparticles were fabricated as indicated in Example 1 and the release buffer was Tris-EDTA 10 mM, pH. 7.4, 0.02% sodium azide.

Methods

Release of plasmid DNA from these nanoparticles was determined using a standard drug release assay. Briefly, 10 mg of the P(FA:SA)-pCMV/βgal nanoparticles were incubated in 0.5 ml of the release buffer at room temperature.

The 0.25 ml of the supernatant was collected and replaced with fresh release buffer periodically and analyzed for the presence of plasmid DNA. The collected supernatant was analyzed at 24 hrs, 72 hrs, 1 week and 2 weeks using agarose gel electrophoresis.

Results

The following samples were analyzed by Agarose gel electrophoresis 1) λ Hind III ladder; 2) stock unencapsulated pCMV/βgal; 3) 24 hours; 4) 72 hours; 5) 1 week; 6) 2 week banding pattern of released plasmid DNA indicated that the plasmids were structurally intact and not degraded. It was observed that the encapsulated pCMV/βgal was released without degradation and was present in the release buffer in open circular and supercoiled conformation. These results indicate that plasmid DNA can be released from the degradable P(FA:SA) nanoparticle formulations.

Example 4

Efficacy of Orally Administered P(FA:SA)-pCMV/βgal Nanoparticles for in vivo Gene Transfer This study was conducted to demonstrate the feasibility of in vivo gene transfer through oral administration of genes incorporated into polymer nanoparticle formulations.

Materials

P(FA:SA)-pCMV/βgal nanoparticles were fabricated as indicated in Example 1 and male Sprague-Dawley rats-400 grams were used for the in vivo evaluation.

Methods

500 μg of unencapsulated pCMV/βgal encapsulated in P(FA:SA) nanoparticles were administered by stomach tube as a single dose to fasted rats. The encapsulated plasmid dosing was given at one-tenth of the control plasmid dose to test the efficacy of the bioadhesive delivery system and demonstrate the protective benefits of encapsulation. The animals were sacrificed after 5 days and the stomach, small intestine and liver were excised and tested for β-galactosidase expression. The small intestine and stomach were carefully rinsed with physiological saline to remove residual food contents and adherent mucus that might falsely elevate background enzyme levels. An additional sample of untreated animals were included as a control to estimate background galactosidase activity. The minimum sample size was 3 animals. Expression of the reporter gene product was assayed by: 1) quantification of β-galactosidase activity and 2) histological identification of transfected cell types using a standard histochemical substrate (X-gal) for β-galactosidase.

Results

A Luminomentry assay of bacterial β-galactosidase activity in tissue homogenates was performed to determine the amount of reporter gene activity detected in the various tissue types following administration of unencapsulated and P(FA:SA) encapsulated pCMV/βgal. Stomach, small intestine and liver were excised from animals fed either pCMV/βgal encapsulated in P(FA:SA) 20:80 "PIN" nanospheres or else the unencapsulated plasmid (control). The tissues were homogenized in lysis buffer containing 0.1% Triton (w/v), PMSF and leupeptin to inhibit proteolysis and incubated at 48° C. for 1 hr to deactivate endogenous β-galactosidase activity. Tissue homogenates were incubated in Galacto-Light substrate and luminescence was measured using a Berthold luminometer.

Five days following a single oral dose of plasmid-loaded PIN nanospheres and unencapsulated pCMV/β-gal, β-galactosidase activity was quantified in the stomach, small intestine and the liver. (FIG. 1) Animals which were fed encapuslated pCMV/β-gal showed significant levels of β-galactosidase activity in both the small intestine and the liver compared to unencapsulated pCMV/β-gal as well as unfed animals. The reporter gene activity measured in animals which received the encapsulated pCMV/β-gal was highest in intestinal tissue (greater than 54 mU compared to 24 mU for the unencapsulated plasmid and 18 mU for the background levels of activity found in untreated control animals). These same animals averaged 11 mU of activity in the liver compared to less than 1 mU for plain CMV-fed or untreated control animals. Reporter gene expression in stomach homogenates was not different and generally low in all groups. The levels in encapsulated and naked plasmid-fed groups were identical at I mU and actually lower than the untreated control levels of 11 mU. The reporter gene expression detected in animals following oral administration of encapsulated pCMV/βgal indicate that the "PIN" system can be utilized to deliver plasmid DNA into intestinal and liver tissues.

Visual localization of transfected cells following oral administration was performed using X-gal histochemical techniques on both whole tissue or frozen sections. Whole tissue staining of intestinal segments from animals receiving encapsulated pCMV/β-gal showed occasional β-galactosidase positive staining of intestinal villous epithelium as well as the outer serosal surface of Peyer's patches. However, it has been shown that some populations of rat intestinal tissue, primarily the epithelial cells on the villous apical tip, contain endogenous lactose which makes differentiation between transfected bacterial β-galactosidase and background activity difficult. Because of the difficulties associated with conclusive identification of transfected cells within intestinal villi, we focused on other cell populations which do not contain background activities, the Peyer's patch.

Whole tissue X-gal staining showed that the serosal surface of small intestine from encapsulated β-galactosidase fed rats stained intensely in localized areas corresponding to areas containing Peyer's patches. Similar histochemical X-gal staining of frozen sections corresponding to the Peyer's patch area revealed that although there were a few (β-galactosidase positive cells within the central lymphoid tissue mass, the majority of transfected cells were located in the muscularis mucosae and advertitia below the Peyer's patch. This distribution of staining was consistent with previous studies which showed retention of nanospheres in the Peyer's patch. Neither groups o(f control animals (unencapsulated pCMV/β-gal or unfed normal rats) showed any false-positive β-galactosidase staining in the Peyer's patches region. Histological examination of the tissue revealed near normal histology in all experimental groups with no evidence of mucosal damage or inflammation.

CONCLUSION

Encapsulation of plasmid DNA in the "PIN" system offers two primary benefits: 1) protection from rapid degradation when administered orally and 2) targeting of transfection to certain cell types. The results of the in vivo study confirmed that plasmid DNA can be delivered by the oral route using the bioadhesive "PIN" nanoparticle formulations. The encapsulated DNA is incorporated into cells in the small intestine and hepatocytes and can express functional gene products at levels that are easily detectable using common histological and luminometric techniques.

Certain of the various objects and advantages of the invention are illustrated in the following examples. Numerous equivalents and embodiments will be apparent to those of ordinary skill in the art and are intended to be embraced by the appended claims.

What we claim is:

1. A method for delivery of a gene under the control of a promoter to a cell of a subject, comprising:

administering to the respiratory tract of a subject by bringing into contact therewith an effective amount of a polymeric microparticle containing an intact vector comprising a gene under the control of a promoter, and wherein the microparticles are prepared by phase inversion microencapsulation.

2. A method for delivery of a gene under the control of a promoter to a cell of a subject, comprising:

administering to the respiratory'tract of a subject by bringing into contact therewith an effective amount of a preparation of polymeric bioadhesive microparticles containing an intact vector comprising a gene under the control of a promoter which is prepared from a freeze-dried gene polymer solution, wherein the freeze-dried gene-polymer solution is prepared by adding the gene to a polymer solution, freezing of the gene-polymer solution, and drying by vacuum of the emulsification containing the gene.

3. A method for delivery of a gene under the control of a promoter to a cell of a subject, comprising:

administering to the respiratory tract of a subject by bringing into contact therewith an effective amount of a polymeric bioadhesive microparticle having an average particle size of between ten nanometers and one micron containing an intact vector comprising a gene under the control of a promoter.

4. The method of anyone of claims 1–3, wherein the gene is delivered to a cell of the respiratory epithelium.

5. The method of anyone of claims 1–3, wherein the gene is delivered systemically.

6. The method of anyone of claims 1–2, wherein the microparticle has an average particle size of between ten nanometers and five microns.

7. The method of anyone of claims 1–2, wherein the microparticle has an average particle size of between one hundred nanometers and three microns.

8. The method of anyone of claims 1–3, wherein the microparticle comprises a polyanhydride.

9. The method of anyone of claims 1–3, wherein the gene encodes an antigen.

10. The method of claim 9, wherein the antigen is selected from the group consisting of a viral antigen and a tumor antigen.

11. The method of anyone of claims 2–3, wherein the microparticle is prepared by phase inversion microencapsulation.

12. The method of anyone of claims 1–3, wherein the microparticle comprises poly(fumaric-co-sebacic) anhydride.

* * * * *

UNITED STATES PATENT AND TRADEMARK OFFICE
CERTIFICATE OF CORRECTION

PATENT NO. : 6,677,313 B1
DATED : January 13, 2004
INVENTOR(S) : Mathiowitz et al.

It is certified that error appears in the above-identified patent and that said Letters Patent is hereby corrected as shown below:

Column 27,
Lines 3, 11 and 23, delete "a cell" and insert -- the respiratory tract --
Line 12, delete "respiratory'tract" and insert -- respiratory tract --.

Signed and Sealed this

Sixth Day of April, 2004

JON W. DUDAS
*Acting Director of the United States Patent and Trademark Office*